(12) United States Patent
Johs et al.

(10) Patent No.: US 8,223,334 B1
(45) Date of Patent: Jul. 17, 2012

(54) METHOD OF IMPROVING ELLIPSOMETRIC AND THE LIKE DATA

(75) Inventors: Blaine D. Johs, Lincoln, NE (US); Martin M. Liphardt, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 405 days.

(21) Appl. No.: 12/586,692

(22) Filed: Sep. 25, 2009

Related U.S. Application Data

(60) Provisional application No. 61/194,241, filed on Sep. 26, 2008.

(51) Int. Cl.
*G01J 4/00* (2006.01)

(52) U.S. Cl. ........................................... 356/369

(58) Field of Classification Search ................ None
See application file for complete search history.

(56) References Cited

U.S. PATENT DOCUMENTS

| | | | | |
|---|---|---|---|---|
| 3,985,447 A * | 10/1976 | Aspnes | ...................... | 356/369 |
| 5,200,796 A * | 4/1993 | Lequime | ...................... | 356/453 |
| 5,210,417 A * | 5/1993 | Grisham et al. | ............ | 250/338.1 |
| 5,548,404 A | 8/1996 | Kupershmidt et al. | ........ | 356/368 |
| 5,608,526 A * | 3/1997 | Piwonka-Corle et al. | .... | 356/369 |
| 5,699,159 A * | 12/1997 | Mason | ........................... | 356/491 |
| 6,522,406 B1 * | 2/2003 | Rovira et al. | .................. | 356/369 |
| 6,721,052 B2 | 4/2004 | Zhao et al. | ..................... | 356/369 |
| 6,804,004 B1 * | 10/2004 | Johs et al. | ...................... | 356/369 |
| 6,822,738 B1 * | 11/2004 | Johs et al. | ...................... | 356/369 |
| 6,831,740 B2 | 12/2004 | Herzinger et al. | ............. | 356/319 |
| 7,054,006 B2 * | 5/2006 | Wang et al. | .................... | 356/369 |
| 7,061,613 B1 * | 6/2006 | Huang et al. | ................... | 356/364 |
| 7,067,819 B2 | 6/2006 | Janik | ............................. | 250/372 |
| 7,151,605 B1 | 12/2006 | Herzinger et al. | ............. | 356/369 |
| 7,158,231 B1 * | 1/2007 | Woollam et al. | ............... | 356/369 |
| 7,245,376 B2 * | 7/2007 | Liphardt et al. | ............... | 356/369 |
| 7,336,359 B1 * | 2/2008 | Simpson et al. | ............... | 356/364 |
| 7,342,661 B2 | 3/2008 | Ebert et al. | ..................... | 356/369 |
| 7,349,079 B2 | 3/2008 | Zhao et al. | ..................... | 356/128 |
| 7,359,052 B2 | 4/2008 | Fielden et al. | ................. | 356/369 |
| 7,405,826 B2 * | 7/2008 | Gibbs et al. | .................... | 356/432 |
| 7,433,037 B2 | 10/2008 | Zhao et al. | ..................... | 356/369 |
| 7,564,552 B2 | 7/2009 | Fielden et al. | ................. | 356/364 |
| 2005/0128482 A1 * | 6/2005 | Gibbs | ........................... | 356/364 |
| 2008/0204750 A1 * | 8/2008 | Rassman et al. | .............. | 356/364 |

* cited by examiner

*Primary Examiner* — Gordon Stock, Jr.
(74) *Attorney, Agent, or Firm* — James D. Welch (57) ABSTRACT

A system and method for improving data provided by ellipsometer, polarimeter and the like systems involving diminishing the effects of undesirable noise in the intensity of a beam of electromagnetic radiation caused by, for instance, random variations in intensity of a source provided beam of electromagnetic radiation and/or periodic or non-periodic variations in beam intensity resulting from wobble/wander of a moving sample, during investigation of the sample by the beam of electromagnetic radiation.

17 Claims, 5 Drawing Sheets

$Sdet_i$ is the signal measured by the ellipsometer detector

FIG. 3a $Ndet_i$ is the signal measured by the "normalizing" detector

FIG. 3b $$Strue_i := \frac{Sdet_i}{Ndet_i}$$

$Strue_i$ is the "true" modulated signal, after normalizing by the light source intensity variations

FIG. 3c $Sdet_i$ is the signal measured by the ellipsometer detector

FIG. 4a $Nscan_i$ is the "normalizing scan" acquired with the ellipsometer modulation disabled

FIG. 4b $$Strue_i := \frac{Sdet_i}{Nscan_i}$$

$Strue_i$ is the "true" modulated signal, after normalizing by the light source intensity variations

FIG. 4c

METHOD OF IMPROVING ELLIPSOMETRIC AND THE LIKE DATA

CROSS-REFERENCE TO OTHER APPLICATIONS

This Application claims Benefit of Provisional Application 61/194,241 Filed Sep. 26, 2008.

TECHNICAL FIELD

The present invention relates to the practice of ellipsometry and polarimetry or the like, and more particularly is a system and method for improving data provided by a sample investigation system involving the diminishing of the effects of undesirable noise in the intensity of a beam of electromagnetic radiation caused by, for instance, random variations in a source of the beam of electromagnetic radiation and/or wander/wobble caused by a moving sample during investigation thereof by a beam of electromagnetic radiation.

BACKGROUND

It is known to investigate samples with beams of electromagnetism using ellipsometer systems. It is also known that unaccounted for changes in the characteristics of a beam of electromagnetic radiation, (ie. noise content), used to investigate a sample can adversely affect the results achievable by practice of ellipsometry.

As it is a particularly relevant area for application of the present invention, it is noted that a benefit of ellipsometry is that data produced thereby consists of a phase angle between, and a ratio of the intensities of, orthogonal components in a polarized beam. As changes in beam intensity generally affect both orthogonal components of the polarized beam, it is generally believed that forming a ratio of the intensities of the orthogonal components cancels out random variations in a beam of electromagnetic radiation provided by the affected source. However, it can occur that, for instance, data detectors operate differently when receiving different intensity signals, thus it can, even in ellipsometry, be of benefit to compensate for changes in intensity of a beam of electromagnetic radiation which interacts with a sample prior to it entering into a data detector. Further, it can occur that source provides electromagnetic radiation having noise with a frequency component which is substantially the same as a frequency at which a beam of electromagnetic radiation is modulated by an ellipsometer. Without some approach to separating the effects thereof from modulation desirably intentionally imposed on beam intensity, the results of analysis of a sample will be in error.

It is also noted that changes in the intensity of a beam of electromagnetic radiation entering a detector can result from not only from changes in output intensity of a source, but can result from said beam being reflected from a sample which is, for instance, rotated during data collection to allow investigation of more than one spot thereon, or has material deposited thereupon during sample investigation which changes the characteristics of a single investigated spot. This effect can be appreciated by realizing that If the sample does not have a truely flat surface and/or is not perfectly aligned and rotated about an axis which is oriented truely normally to an investigated surface thereof, differing amounts of incident electromagnetic radiation will reflectively enter a data detector therefrom, depending on at what point in a sample rotation cycle said sample is investigated. And, depositing material onto a sample also changes the amount of incident electromagnetic radiation will reflectively enter a data detector. Similar effects can result when a sample is caused to undergo a linear motion, such as when a ribbon sample is unwound from one spool and wound onto another, with the beam of electromagnetic radiation being directed to interact with said ribbon sample at a point between said spools. It is noted that identified noise can then be random and/or periodic.

A relevant identified U.S. Pat. No. 7,342,661 to Ebert et al. Said 661 patent describes a normalization procedure for data in a rotating element ellipsometer system involving applying D.C. components from half cycles to, respectively, normalize data in said half cycles. U.S. Pat. Nos. 7,151,605 and 6,831,740 to Herzinger et al., describe methodology for efficiently providing good data of improved precision over a range of wavelengths.

Other relevant art includes dual channel ellipsometers, such as described in U.S. Pat. Nos. 7,564,552; 7,433,037; 7,359,052; 7,349,079; 7,067,819; 6,721,052 and 5,548,404. In it disclosed that a difference between such dual channel systems and the present invention is that the former typically normalizes an overall signal average by a reference detector signal, while the present invention teaches that every data point is separately normalized. Normalizing each data point separately can lead to, for instance, determining Fourier coefficients which are extracted form an ellipsometer signal with improved precision and accuracy. This, in turn, leads to improved accuracy in ellipsometric data.

A system which comprises means for compensating undesired "noise" caused by changes in electromagnetic beam intensity entering a detector, (such as those resulting from random source output variation and those resulting from typically periodic sample movement), in ellipsometers, polarimeters or the like, and the methodology of its application, would therefore provide utility. The present invention provides methods for improving the precision and accuracy of ellipsometric data by normalizing a "true data" containing signal to unintended variations in beam intensity which are not the result of intended applied modulation in the ellipsometer system, such as are caused by variations in beam source intensity and/or by a moving substrate.

DISCLOSURE OF THE INVENTION

The present invention is a method of normalizing an electromagnetic signal which contains both:
  desirable modulated information content; and
  undesirable noise content;
to the undesirable noise content therein, to substantially eliminate the effects thereof, and provide substantially only the desirable (true) modulated information per se.
  Said method comprises the steps of:
  a) providing a sample investigation system comprising:
    a source of a beam of electromagnetic radiation;
    a functionally removable polarization state generator;
    a stage for supporting, and optionally controlling a position and orientation of a sample;
    a functionally removable polarization state analyzer; and
    a data detector.
  It is noted that the functionally removable polarization state generator and functionally removable polarization state analyzer serve to impose modulation on desirable information content when functional, but have do not do so when not functional. Further, in use, a portion of a beam of electromagnetic radiation provided by said source thereof interacts with a sample on said stage for supporting a sample and enters said data detector, which produces non-normalized data containing desirable modulated information content.

Said sample investigation system further comprises:
means for producing data representing undesirable noise content in a beam of electromagnetic radiation provided by said source thereof, and detected by said data detector after it interacts with said sample, said undesirable noise content being random, periodic or a combination thereof, and said system also further comprises:
a computer system for receiving and storing input data representing undesirable noise content, as well as non-normalized data containing desirable modulated information content.

(Note: said undesirable noise content can result from variation in said source output intensity and/or from sample motion movement).

Said method further comprises steps b and c, wherein said steps are:
b) causing a beam of electromagnetic radiation to exit said source thereof such that:
a portion thereof interacts with a surface of a sample which is present on said stage for supporting a sample and enters said data detector, such that non-normalized data containing desirable modulated information content versus time is produced, and entered into said computer; and
either simultaneously with or sequentially after, or before a portion thereof interacts with said means for producing data representing undesirable noise content such that undesirable noise content data versus time is produced and entered into said computer;
c) causing said computer to perform a selection from the group consisting of:
sequentially, time point by time point, normalize said non-normalized data containing desirable modulated information content to said undesirable noise content; and
performing a frequency domain transformation on the time domain non-normalized desirable data containing modulated information content and undesirable noise content data and normalize said non-normalized desirable data containing modulated information content to said undesirable noise content data.

The result is that non-normalized data containing desirable modulated information content is normalized to the undesirable noise content data, thereby substantially eliminating the effect of undesired noise content on said desirable modulated information content.

Said method can also comprise:
d) said method further comprising performing at least one selection from the group consisting of:
storing at least some data provided by said data detector in machine readable media;
analyzing at least some of the data provided by said data detector and storing at least some of the results of said analysis in machine readable media;
displaying at least some data provided by said data detector by electronic and/or non-electronic means;
analyzing at least some of the data provided by said data detector and displaying at least some of the results of said analysis by electronic and/or non-electronic means;
causing at least some data provided by said data detector to produce a signal which is applied to provide a concrete and tangible result;
analyzing at least some of the data provided by said data detector and causing at least some thereof to produce a signal which is applied to provide a concrete and tangible result.

Said method can provide that the means for producing data which represents undesirable noise content in a beam of electromagnetic radiation in said sample investigation system provided in step a comprise a source normalizing detector which is positioned to intercept a portion of the beam of electromagnetic radiation as provided by said source thereof. This interception can be direct or via a reflecting means for reflecting electromagnetic radiation. Further, it is said source normalizing detector which provides undesirable random noise content data to said computer system in step b simultaneous with production of non-normalized data containing desired modulated information content versus time, which is also entered into said computer in step b.

Said method can alternatively provide that the means for producing data representing undesirable noise content in a beam of electromagnetic radiation in said sample investigation system provided in step a, comprising a beam splitter placed in the locus of said beam of electromagnetic radiation provided by said source thereof, and a source normalizing detector which is positioned to intercept a portion of the beam of electromagnetic radiation which is directed thereinto by said beam splitter; and it is said source normalizing detector which provides undesirable random noise content data to said computer system in step b simultaneous with production of non-normalized data containing desired modulated information content versus time, which is also entered into said computer in step b.

In any configuration said sample investigating system can further comprise a shutter positioned to block electromagnetic radiation access to said source normalizing detector when desired, and/or further comprise a means for flowing a gas over said source normalizing detector when desired.

It is specifically noted that undesirable noise data can be caused by source intensity variations, and/or by sample movement.

Continuing, said method can provide that the means for producing data representing undesirable noise content in a beam of electromagnetic radiation in said sample investigation system provided in step a, comprise the data detector. In this case said stage causes said sample to move, and two sets of data are obtained sequentially, in either order, from said data detector. One said set of data comprises desirable modulated information content is obtained with said functionally removable polarization state generator and said functionally removable polarization state analyzer provided in step a functioning, and the other said set of data corresponds to undesirable noise and is obtained with said functionally removable polarization state generator and said functionally removable polarization state analyzer being functionally removed.

It is said data set obtained with said functionally removable polarization state generator and said functionally removable polarization state analyzer being functionally removed which provides undesirable noise content data to said computer system in step b. Sequentially obtained non-normalized data containing desirable modulated information content versus time is also entered into said computer in step b.

Where sample movement is present, it can comprise a precession rotation about an axis projecting from said investigated sample surface, and when this is the case, said undesirable noise data is periodic with said period being a time period corresponding to full rotation of said sample. Where the sample movement is not rotational, it is noted that the undesirable noise data can be periodic and/or not periodic.

Said method can involve the sample investigation system provided in step a further comprising a source normalizing detector which is positioned as a selection from the group consisting of:

it intercepts a portion of the beam of electromagnetic radiation as provided by said source thereof; and it intercepts a portion of the beam of electromagnetic radiation as provided by said source thereof via a provided beam splitter; and said stage can also cause said sample to move while the data detector receives input; such that, as regards variation in source intensity, said source normalizing detector provides undesirable noise intensity vs time data to said computer system in step b; and such that as regards sample movement the means for producing data representing undesirable noise content in a beam of electromagnetic radiation provided in step a comprises the data detector, and wherein said stage causes said sample to move, and wherein two sets of data are sequentially, in either order, obtained from said data detector.

One said set of said data comprises desirable modulated information content and being obtained with said functionally removable polarization state generator and said functionally removable polarization state analyzer provided in step a functioning, and the other said set of said data corresponds to undesirable noise and being obtained with said functionally removable polarization state generator and said functionally removable polarization state analyzer being functionally removed. It is noted that it is said data set obtained with said functionally removable polarization state generator and said functionally removable polarization state analyzer being functionally removed which provides undesirable noise content data to said computer system in step b, along with sequentially obtained non-normalized data containing desirable modulated information content versus time, which is also entered into said computer in step b. In step c, then, the computer is caused to sequentially, time point by time point or an equivalent procedure in the frequency domain, normalize said non-normalized data containing desirable modulated information content to said undesirable noise content data representing both variation in source intensity, and sample movement. It is noted that a preferred approach to normalizing frequency domain data can involve normalizing Fourier Coefficients corresponding to non-normalized data containing desirable modulated information content to those corresponding to undesirable noise content data. Further, Fourier Coefficients corresponding to a 2 w signal are typically, but not exclusively, the most important. It is also possible to acquire a plurality of data sets corresponding to undesirable noise content and an average thereof applied in the normalization process.

It is to be appreciated that the methodology can involve said computer controlling operation of said sample investigation system in steps b-d.

It is stated for clarity that undesirable noise content data, and non-normalized data containing desirable modulated information content must be synchronized. For instance, where a sample is rotated and data is acquired for both the situation where modulation is applied to the electromagnetic beam and when it is not, it is required that the data sets be synchronized so that non-normalized data containing desirable modulated information content is normalized to the undesirable noise content data corresponding to the same point in sample rotation. This can be accomplished by application of a synchronization pulse to mark data sets when a specific sample position is known.

It is also disclosed that the present invention can be applied as a quality control indicator. That is, if a normalizing detector signal detects variation in intensity of a beam source, the corresponding non-normalized data containing desirable modulated information content can be discarded and the data reacquired.

The present invention will be better understood by reference to the Detailed Description Section of this Specification, in conjunction with the Drawings.

BRIEF DESCRIPTION OF THE DRAWINGS

FIG. 2a shows a present invention system comprising a sample which precesses when is rotated.

FIG. 2b1 demonstrates the effect of rotating sample precession at the location of an aperture prior to a polarization state analyzer.

FIG. 2b2 demonstrates the effect of sample movement based on unwinding and winding from and onto reels.

FIGS. 2e1, 2e2 and 2e3 show possible approaches to intercepting a portion of a beam of electromagnetic radiation which exits said source, involving application of a shutter.

FIGS. 2f1 and 2f2 show two possible approaches to intercepting a portion of a beam of electromagnetic radiation which exits said source, involving application of a means for flowing gas over elements involved.

FIG. 3b shows representative data provided by a source normalizing detector during the acquisition of the data shown in FIG. 3a.

DETAILED DESCRIPTION

Figure 1A:
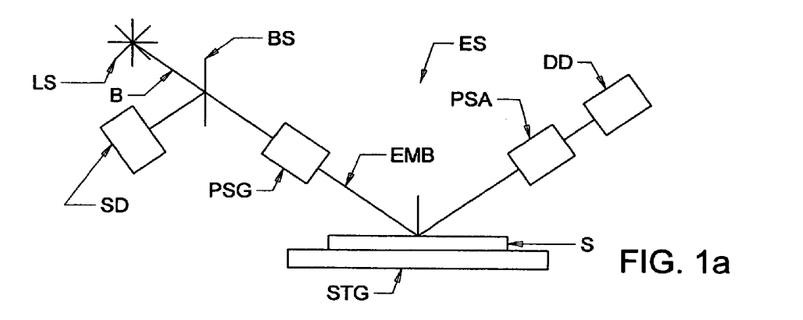
FIG. 1a shows a present invention system including a beam splitter for providing source electromagnetism to a source normalizing detector.
Figure 1B:
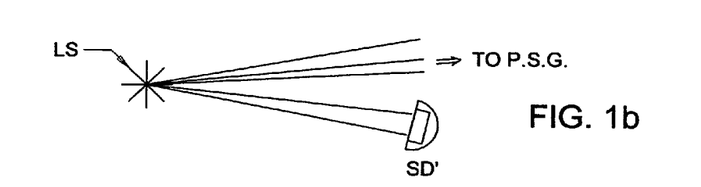
FIG. 1b shows that the beam splitter in FIG. 1 can be replaced by an appropriately positioned source normalizing detector.

Turning now to the Drawings, FIG. 1a demonstrates a preferred present invention System (ES) for compensating effects of Source (LS) intensity variation, including a beam splitter (BS) for directing a portion of Source (LS) provided electromagnetism to a Source Normalizing Detector (SD). Also indicated are that the Source (LS) provides a Beam (B) of Electromagnetic Radiation which passes through a Polarization State Generator (PSG), emerges therefrom as beam (EMBJ, (also shown in FIG. 2a) and interacts with a Sample (S) present on a Stage (STG) for Supporting said Sample (S), then passes through a Polarization State Analyzer (PSA) and into the Data Detector (DD). FIG. 1b shows that the Beam Splitter (BS) in FIG. 1 can be replaced by an appropriately positioned Source Normalizing Detector (SD') which directly intercepts a portion of the Beam (B) of Electromagnetic Radiation. Either approach, (ie. using or not using a Beam Splitter (BS)), for detecting a portion of the Beam (B), can be applied. It is to be appreciated that the Source Normalizing Detectors (SD) or (SD') are positioned before the Polarization State Generator (PSG).

Figures 2A, 2B, 2B:
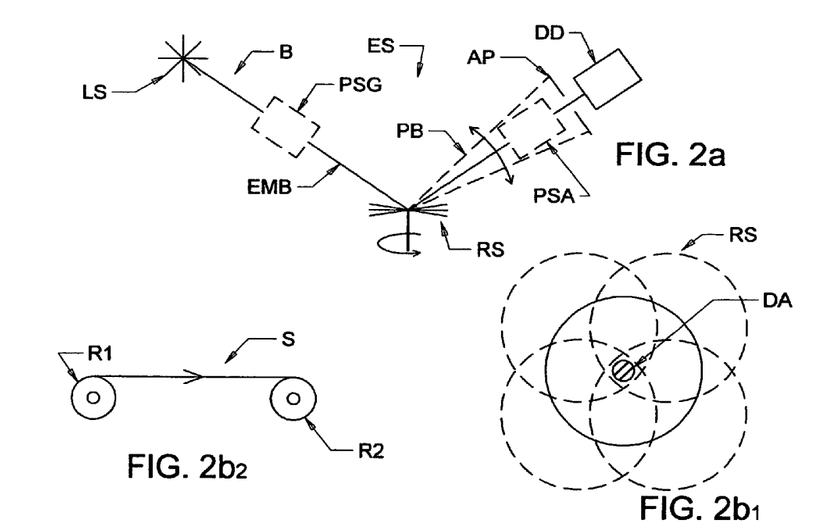

FIG. 2a demonstrates a preferred present invention System (ES) which is generally similar to that in FIG. 1a, but arranged for application in compensating the effects of a Rotating Sample (RS) which precesses when it is rotated, as evidenced by a reflected Precessing Beam (PB). Note that the Polarization State Generator (PSG) and Polarization State Analyzer (PSA) are indicated in dashed lines, as being optional. That is, their function can be enabled or disabled, or they can be placed in, and removed from the positions shown as appropriate for obtaining sample composition analysis data, or sample precession data. This capability enables practicing the Method steps disclosed in the Disclosure of the Invention Section related to normalizing non-normalized data containing desirable modulated information content in a data set, to a data set containing undesirable noise content.

Figure 2C:
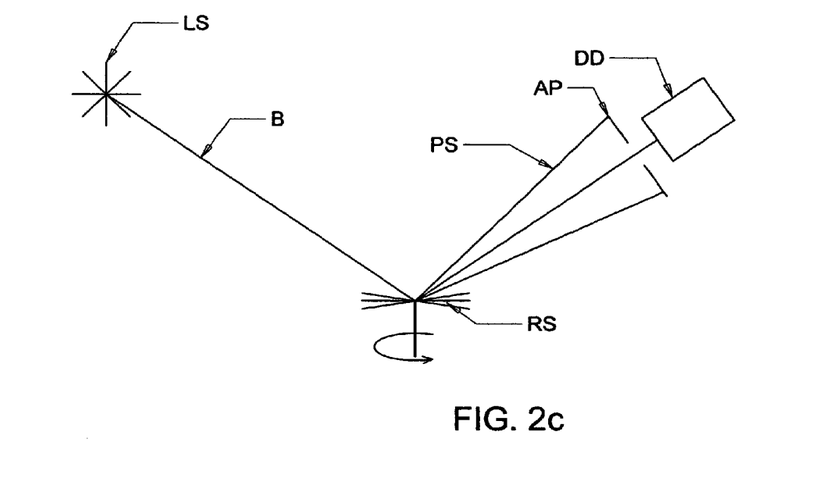
FIG. 2c demonstrates a that the polarization state generating and analyzing elements can be removed or made functionally inoperable.

FIG. 2b1 demonstrates the effect of rotating Sample (S) precession. Note the presence of functionally a removable Polarization State Generator (PSG) and Polarization State Analyzer (PSA) including a typically functionally removable Aperture (DA)((AP) as in FIG. 2a). FIG. 2c shows the system of FIG. 2b1 with the Polarization State Generator (PSG) and Polarization State Analyzer (PSA) functionally removed. For insight it is noted that, in use, the configuration of FIG. 2a is used to obtain data for characterizing a sample, and FIG. 2c shows a configuration for obtaining a data set that can used to normalize the sample characterizing data set for sample movement (eg. rotational precession (PS) "wobble"). FIG. 2b2 demonstrates that sample (S) motion can be the effect of, for instance, unwinding from and winding onto, respectively, reels (R1) (R2).

Figure 2D:
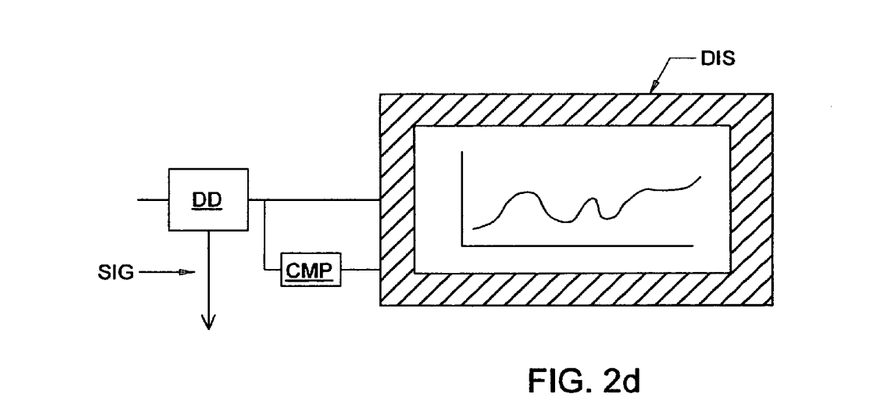
FIG. 2d demonstrates a computer (CMP) can be present in the systems of FIGS. 2a and 2c.

FIG. 2d demonstrates a Computer (CMP) can be present to receive input from the Data Detector (DD) and provide an output signal (SIG), as well as provide input to a Computer (CMP) which can output a Control Signal (CSIG) and can drive Display (DIS) of Data Detector (DD) output, or results of analysis thereof, and/or control operation of the sample investigation system.

Figure 2E:
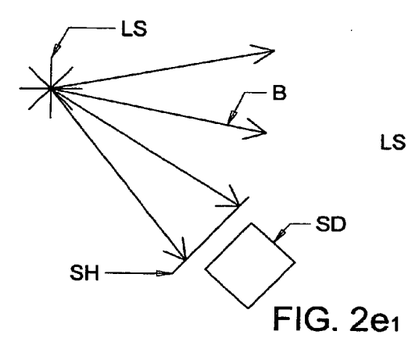
Figure 2E:
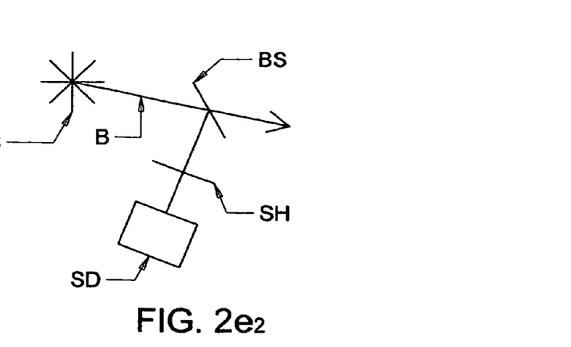
Figures 2E, 2F, 2F:
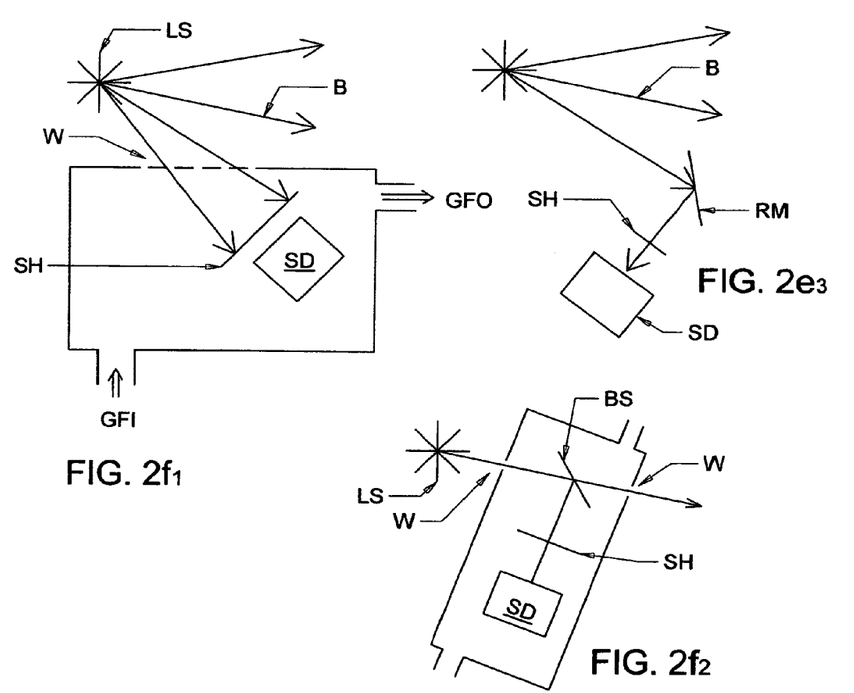

FIGS. 2e1 and 2e1 show two possible approaches to intercepting a portion of a beam of electromagnetic radiation which exits said source, involving application of a shutter (SG). FIG. 2e3 shows a reflector (RM) can be included to direct a portion of the electromagnetic radiation exiting the Source (LS) into the Source Detector (SD).

FIGS. 2f1 and 2f2 show two possible approaches to intercepting a portion of a beam of electromagnetic radiation, (W is an opening), which exits said source (LS), involving application of a means for flowing gas over elements involved. Shown are Gas Flow In (GFI) and Gas Flow Out (GFO) of a containment in which is present a Source Normalizing Detector (SD).

Figure 3A:
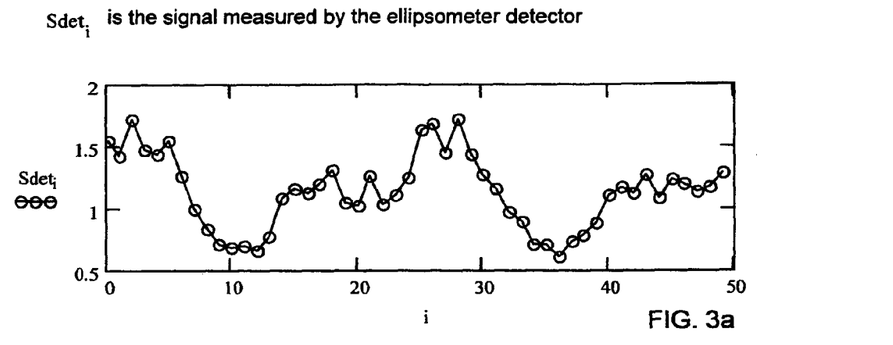
FIG. 3a shows representative data provided a data detector when applying the system of FIG. 1a or 1b to investigate a sample.

FIG. 3a shows representative data provided a Data Detector (DD) when applying the System (ES) of FIG. 1a or 1b to investigate a Sample (S). That is, the FIG. 3b data can be acquired by application of a Beam Splitter (BS) to direct the Beam (B) of Electromagnetic Radiation to the Source Normalizing Detector (SD), or the Source Normalizing Detector (SD) can be positioned to directly access a portion of the Beam (B).

Figure 3B:
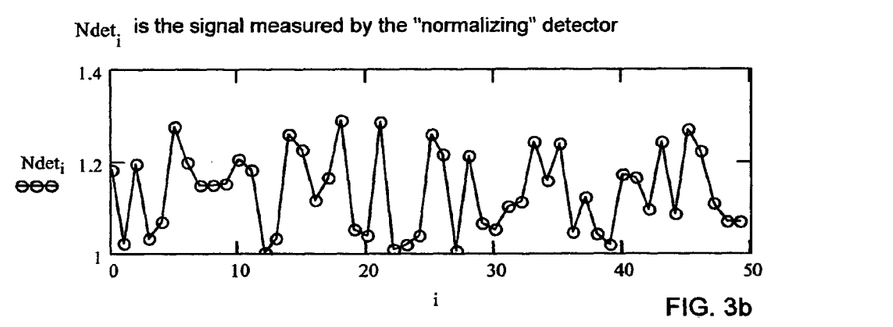

FIG. 3b shows representative data provided by a Source Normalizing Detector (SD) during the acquisition of the data shown in FIG. 3a.

Figure 3C:
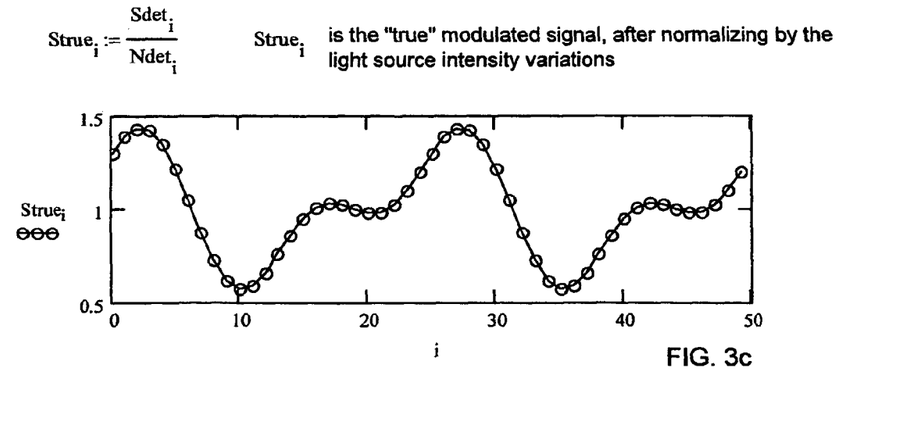
FIG. 3c shows the data of FIG. 3a normalized to that in FIG. 3b.

FIG. 3c shows the data of FIG. 3a normalized to that in FIG. 3b. Note the improved nature of the FIG. 3c data as compared to the FIG. 3a data. Also note that the governing equation for normalization is presented as:

$$Strue_i = (Sdet_i)/(Ndet_1);$$

which serves to indicate that corresponding synchronized data representing:
non-normalized data containing desirable modulated information content ($Sdet_i$) shown in FIG. 3a;
is divided by data representing:
undesirable noise content ($Ndet_i$) shown in FIG. 3b;
thereby substantially eliminating the effect of undesired noise content on said desirable modulated information content $Strue_i$. FIGS. 3a-3c demonstrate a large 20% variation in beam intensity provided by a source, but the present invention can be applied to any level of intensity variation. Further, while the data shown correspond to a single modulation cycle, the present invention method can be applied over any time range of signal sampling. Further, it is to be understood that Fourier coefficients can be extracted from normalizing noise content data and used to correct corresponding Fourier coefficients in non-normalized data containing desirable modulated information content.

Figure 4A:
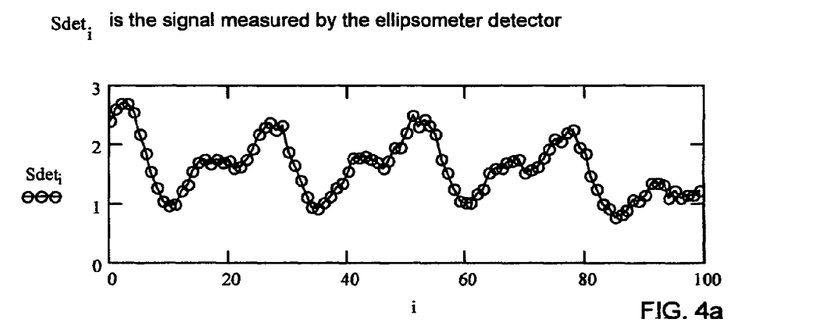
FIG. 4a shows representative data provided a data detector when applying the system of FIG. 2a to investigate a sample, with the polarization state generator enabled.

FIG. 4a shows representative data provided a Data Detector as in FIG. 2a, when applying the System (ES) of FIG. 2a to investigate a Sample (S), with the Polarization State Generator (PSG) enabled to effect a modulated beam.

Figure 4B:
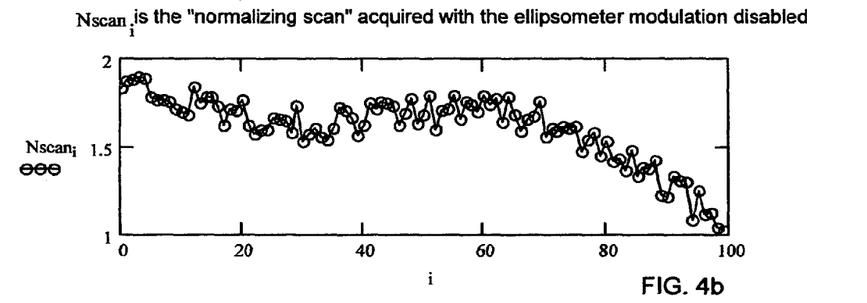
FIG. 4b shows representative data provided a data detector when applying the system of FIG. 2a to investigate a sample, with the polarization state generator disabled.

FIG. 4b shows representative data provided a data detector when applying the ellipsometer system of FIG. 2a to investigate a sample, with the polarization state generator disabled.

Figure 4C:
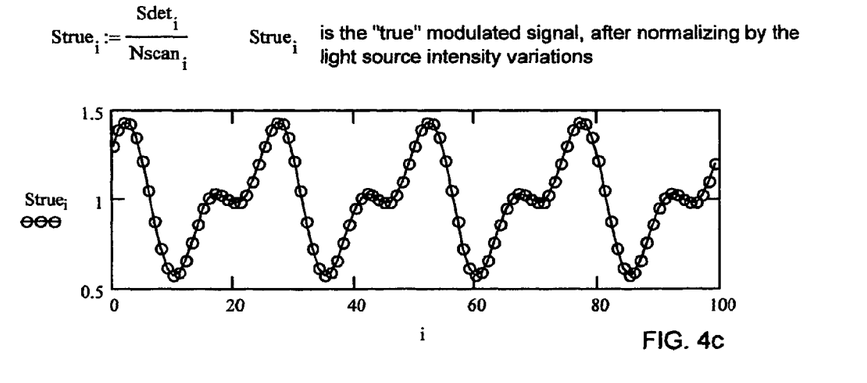
FIG. 4c shows the data of FIG. 4a normalized to that in FIG. 4b.

FIG. 4c shows the data of FIG. 4a normalized to that in FIG. 4b. Note the improved nature of the FIG. 4c data as compared to the FIG. 4a data. Also note that the governing equation for normalization is presented as:

$$Strue_i = (Sdet_i)/(Nscan_i);$$

which serves to indicate that corresponding synchronized data representing:
non-normalized data containing desirable modulated information content ($Sdet_i$) shown in FIG. 4a;
is divided by data representing:
undesirable noise content ($Nscan_i$) shown in FIG. 4b;
thereby substantially eliminating the effect of undesired noise content on said desirable modulated information content $Strue_i$.

Note that the use of the subscript "i" serves to indicate that corresponding undesirable noise content data is applied to non-normalized data containing desirable modulated information content, whether the normalization is carried out in the time or frequency domain. This can result from synchronization in the time domain, or the result of comparing like Fourier Coefficients in the frequency domain.

It is noted that the embodiments of the System (ES) shown in FIGS. 1a & 1b and 2a are preferred for use in compensating for Source (LS).

While the present invention is useful in any approach to data analysis, it is particularly applicable where data analysis involves extraction of Fourier Coefficients from said data.

In this Specification and in the Claims, the terminology "ellipsometer" or "ellipsometry" and the like, is to be read to include "polarimeter" or "polarimetry", and all such terminology is incorporated into the generic terminology "sample investigation system".

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of normalizing an electromagnetic signal which contains both:
   desirable modulated information content; and
   undesirable noise content;
   to the undesirable noise content to substantially eliminate effects thereof, and provide desirable modulated information per se;
   said method comprising the steps of:
   a) providing a sample investigation system comprising:
      a source of a beam of electromagnetic radiation;
      a functionally removable polarization state generator;
      a stage for supporting, and controlling a position and orientation of a sample;
      a functionally removable polarization state analyzer; and
      a data detector;
   which functionally removable polarization state generator and functionally removable polarization state analyzer serve to impose modulation on desirable information content when functional; and such that in use a portion of a beam of electromagnetic radiation provided by said source thereof interacts with a sample on said stage for supporting a sample and enters said data detector, which produces non-normalized data containing desirable modulated information content;
   said sample investigation system further comprising:
      means for producing data representing undesirable noise content in a beam of electromagnetic radiation provided by said source thereof and detected by said data detector after said beam of electromagnetic radiation interacts with said sample, said undesirable noise content being random, periodic or a combination thereof; and
   said sample investigation system also further comprising:
      a computer system for receiving and storing input data representing undesirable noise content, as well as non-normalized data containing desirable modulated information content;
   b) causing a beam of electromagnetic radiation to exit said source thereof such that:
      a portion thereof interacts with a surface of a sample which is present on said stage for supporting a sample and enters said data detector, such that non-normalized data containing desirable modulated information content versus time is produced, and entered into said computer system; and
      a portion thereof at a time selected from the group consisting of:
         before;
         simultaneously with; and
         sequentially after,
      said non-normalized data containing desirable modulated information content versus time is produced, and entered into said computer system, interacts with said means for producing data representing undesirable noise content, such that undesirable noise content data versus time is produced and entered into said computer system;
   c) causing said computer system to perform a selection from the group consisting of:
      sequentially, time point by time point, normalize said non-normalized data containing desirable modulated information content to said undesirable noise content data; and
      performing a frequency domain transformation on the time domain non-normalized data;
   containing desirable modulated information content and undesirable noise content data and normalize said non-normalized data containing desirable modulated information content to said undesirable noise content data;
   to the end that the non-normalized data containing desirable modulated information content is normalized to the undesirable noise content data, thereby substantially eliminating an effect of undesired noise content on said desirable modulated information content.

2. A method as in claim 1 wherein said undesirable noise content results from:
   variation in said source output intensity, and/or
   sample movement.

3. A method as in claim 1 wherein said sample investigation system provided in step a) further comprises a source normalizing detector which is positioned as a selection from the group consisting of:
   it intercepts a portion of the beam of electromagnetic radiation as provided by said source thereof; and
   it intercepts a portion of the beam of electromagnetic radiation as provided by said source thereof via a provided beam splitter; and
   wherein said stage causes said sample to move while the data detector receives input;
      such that, as regards variation in source intensity, said source normalizing detector provides undesirable noise intensity versus time data to said computer system in step b); and
   such that as regards sample movement the means for producing data representing undesirable noise content in a beam of electromagnetic radiation provided in step a) comprises the data detector, and wherein said stage causes said sample to move, and wherein two sets of data are sequentially, in either order, obtained from said data detector:
      one said set of data comprising desirable modulated information content and being obtained with said functionally removable polarization state generator and said functionally removable polarization state analyzer provided in step a functioning; and
      the other said set of data corresponding to undesirable noise and being obtained with said functionally removable polarization state generator and said functionally removable polarization state analyzer being functionally removed;
   wherein it is said data set obtained with said functionally removable polarization state generator and said functionally removable polarization state analyzer being functionally removed which provides undesirable noise content data to said computer system in step b), along with sequentially obtained non-normalized data containing desirable modulated information content versus time, which is also entered into said computer system in step b);
   such that in step c) the computer system is caused to normalize said non-normalized data containing desirable modulated information content to said undesirable noise content data representing both variation in source intensity, and sample movement.

4. A method as in claim 1 in which said computer system further controls operation of said sample investigation system in steps b) and c).

5. A method as in claim 1, which further comprises the step of:
   d) said method comprising performing at least one selection from the group consisting of:
   storing at least some data provided by said data detector in machine readable media;
   analyzing at least some data provided by said data detector and storing at least some results of said analysis in machine readable media;
   displaying at least some data provided by said data detector by a display;
   analyzing at least some data provided by said data detector and displaying at least some results of said analysis by a display;
   causing at least some data provided by said data detector to produce a signal which is applied to provide a physical result;
   analyzing at least some data provided by said data detector and causing at least some thereof to produce a signal which is applied to provide a physical result.

6. A method as in claim 1, in which the means for producing data representing undesirable noise content in a beam of electromagnetic radiation in said sample investigation system provided in step a), comprises a source normalizing detector which is positioned to intercept a portion of the beam of electromagnetic radiation as provided by said source thereof directly or via a reflector for reflecting electromagnetic radiation; and it is said source normalizing detector which provides undesirable random noise content data to said computer system in step b) simultaneous with production of non-normalized data containing desirable modulated information content versus time, which is also entered into said computer system in step b).

7. A method as in claim 1, in which the means for producing data representing undesirable noise content in a beam of electromagnetic radiation in said sample investigation system provided in step a), comprises a beam splitter placed in a locus of said beam of electromagnetic radiation provided by said source thereof, and a source normalizing detector which is positioned to intercept a portion of the beam of electromagnetic radiation which is directed thereinto by said beam splitter; and it is said source normalizing detector which provides undesirable random noise content data to said computer system in step b) simultaneous with production of non-normalized data containing desirable modulated information content versus time, which is also entered into said computer system in step b).

8. A method as in claim 1, in which the means for producing data representing undesirable noise content in a beam of electromagnetic radiation in said sample investigation system provided in step a, comprises the data detector, and wherein said stage causes said sample to move, and wherein two sets of data are sequentially, in either order, obtained from said data detector:
   one said set of data comprising desirable modulated information content and being obtained with said functionally removable polarization state generator and said functionally removable polarization state analyzer provided in step a functioning; and
   the other said set of data corresponding to undesirable noise and being obtained with said functionally removable polarization state generator and said functionally removable polarization state analyzer being functionally removed;
   wherein it is said data set obtained with said functionally removable polarization state generator and said functionally removable polarization state analyzer being functionally removed which provides undesirable noise content data to said computer system in step b), along with sequentially obtained desirable non-normalized modulated information content versus time, which is also entered into said computer system in step b).

9. A method as in claim 6 where said sample investigating system further comprises a shutter positioned to block electromagnetic radiation access to said source normalizing detector when desired.

10. A method as in claim 6 where said sample investigating system further comprises a system for flowing a gas over said source normalizing detector when desired.

11. A method as in claim 6 wherein the undesirable noise data is caused by source intensity variations.

12. A method as in claim 7 where said sample investigating system further comprises a shutter positioned to block electromagnetic radiation access to said source normalizing detector when desired.

13. A method as in claim 7 where said sample investigating system further comprises a system for flowing a gas over said beam splitter and/or said source normalizing detector when desired.

14. A method as in claim 7 wherein the undesirable noise data is caused by source intensity variations.

15. A method as in claim 8, wherein the sample movement is a precession rotation about an axis projecting from said investigated sample surface, and said undesirable noise data is periodic, with said period being a time period corresponding to full rotation of said sample.

16. A method as in claim 8, wherein the sample movement is not rotational the undesirable noise data is a selection from the group consisting of:
   periodic; and
   not periodic.

17. A method as in claim 8, in which a plurality of data sets which are not subjected to effects of said polarization state generator are produced, and therefrom producing, an average data set which is an average of said plurality of data sets, said average data set being applied as a representation of the undesirable noise content.

* * * * *